United States Patent
Wahlberg et al.

(10) Patent No.: US 10,799,169 B2
(45) Date of Patent: Oct. 13, 2020

(54) APPARATUS, SYSTEM AND METHOD FOR DETECTING ONSET AUTISM SPECTRUM DISORDER VIA A PORTABLE DEVICE

(71) Applicant: Timothy J. Wahlberg, Geneva, IL (US)

(72) Inventors: Timothy J. Wahlberg, Geneva, IL (US); John M. Martin, Glen Ellyn, IL (US); Chuck Penzone, Oswego, IL (US)

(73) Assignee: Timothy J. Wahlberg, Geneva, IL (US)

( * ) Notice: Subject to any disclaimer, the term of this patent is extended or adjusted under 35 U.S.C. 154(b) by 208 days.

(21) Appl. No.: 16/004,293

(22) Filed: Jun. 8, 2018

(65) Prior Publication Data

US 2019/0374149 A1  Dec. 12, 2019

(51) Int. Cl.
| | |
|---|---|
| *A61B 5/0205* | (2006.01) |
| *A61B 5/16* | (2006.01) |
| *A61B 5/1455* | (2006.01) |
| *A61B 5/00* | (2006.01) |
| *A61B 5/11* | (2006.01) |
| *A61B 7/02* | (2006.01) |
| *A61B 5/0456* | (2006.01) |
| *A61B 5/024* | (2006.01) |

(52) U.S. Cl.
CPC .......... *A61B 5/167* (2013.01); *A61B 5/0205* (2013.01); *A61B 5/0456* (2013.01); *A61B 5/1112* (2013.01); *A61B 5/14551* (2013.01); *A61B 5/7257* (2013.01); *A61B 5/7445* (2013.01); *A61B 7/02* (2013.01); *A61B 5/02416* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 8,669,864 B1* | 3/2014 | Tedesco | G08B 21/0453 340/539.12 |
| 9,560,967 B2* | 2/2017 | Hyde | A61B 5/0002 |
| 2002/0060630 A1* | 5/2002 | Power | A61B 5/1124 340/573.1 |
| 2013/0035579 A1* | 2/2013 | Le | A61B 5/04012 600/383 |

(Continued)

*Primary Examiner* — Kennedy Schaetzle
(74) *Attorney, Agent, or Firm* — Loza & Loza, LLP; Peter Zura (57) ABSTRACT

Technologies and techniques for detecting and alerting onset Autism Spectrum Disorder (ASD), where a device receives sensor data including heart rate data, accelerometer data and audio data. The device is configured to activate the collection of accelerometer data and extract accelerometer data features comprising frequency components if the heart rate exceeds a first threshold, activate the collection of audio data and extract audio data features comprising frequency components if the heart rate data meets or exceeds a second predetermined threshold, determine if the audio data meets or exceeds a predetermined audio threshold comprising frequency characteristics, and transmit an alert indicating the detection of an onset ASD episode, based on the extracted audio data features, the extracted accelerometer data features and the heart rate data.

20 Claims, 8 Drawing Sheets

(56) References Cited

U.S. PATENT DOCUMENTS

| | | | | |
|---|---|---|---|---|
| 2013/0079602 A1* | 3/2013 | Picard | ................. | A61B 5/0022 |
| | | | | 600/301 |
| 2013/0245396 A1* | 9/2013 | Berman | ............. | G06F 19/3418 |
| | | | | 600/301 |
| 2013/0267760 A1* | 10/2013 | Jin | ........................ | A61N 2/004 |
| | | | | 600/9 |
| 2013/0281798 A1* | 10/2013 | Rau | ..................... | A61B 5/4884 |
| | | | | 600/301 |
| 2017/0340270 A1* | 11/2017 | Ganesh | ................. | G16H 40/67 |
| 2018/0078187 A1* | 3/2018 | Anwar | ................... | A61B 5/486 |
| 2018/0117274 A1* | 5/2018 | Porges | .................. | A61B 5/486 |
| 2018/0184964 A1* | 7/2018 | Simon | ..................... | H04W 4/70 |
| 2019/0298244 A1* | 10/2019 | Arai | ..................... | A61B 5/4064 |
| 2019/0374149 A1* | 12/2019 | Wahlberg | ................ | A61B 7/02 |

\* cited by examiner

APPARATUS, SYSTEM AND METHOD FOR DETECTING ONSET AUTISM SPECTRUM DISORDER VIA A PORTABLE DEVICE

FIELD OF TECHNOLOGY

The present disclosure is directed to technologies and techniques for detecting onset Autism Spectrum Disorder via a portable device. More specifically, the present disclosure is directed to detecting user characteristics in a tiered configuration to improve detection of onset Autism Spectrum Disorder, while improving efficiency of the portable device during the course of the detection.

BACKGROUND

Autism Spectrum Disorder (ASD) is a neurodevelopmental disorder characterized by persistent difficulties in social communication, social interaction, and restricted, repetitive patterns of behavior, interests, or activities that are present in the early developmental period. ASD refers to a spectrum of disorders with a range of manifestations that can occur on different degrees and in a variety of forms. To address the many challenges faced by children and adults with ASD, the role of sensing technologies has increased in recent years. These technologies are generally aimed at providing assistance in overcoming these limitations, allowing such individuals to understand and participate in the world around them. Because ASD is not a neurodegenerative disorder, many of the core symptoms can improve as the individuals learn to cope with their environments under the right conditions. The earlier the age at which intervention can be started, the better their learning and daily function can be facilitated. Hence, sensing technologies can play a key role in the screening and therapy of ASD, thus potentially improving the lives of those on the spectrum.

Of the existing sensor-based systems, many provide certain benefits for detecting ASD in users. However, many of these systems utilize expensive sensors and/or equipment that are not practical for home use. Some systems utilize smart phones as a means to process sensor data to detect ASD. However, existing smart phone based ASD systems can be inaccurate and are not computationally efficient, resulting in slower smart phone function during sensing operations. Additionally, the inefficient utilization of phone sensors (e.g., camera, fingerprint scanner, microphone) often causes excessive drain on the smart phone battery, which may result in periods of inoperability for the phone. What is needed are technologies and techniques for accurately detecting ASD while increasing efficiency for a portable monitoring device.

SUMMARY

Various apparatus, systems and methods are disclosed herein relating to detecting onset ASD in a tiered manner.

In some illustrative embodiments, a system is disclosed, for detecting and alerting onset Autism Spectrum Disorder (ASD), comprising a processing apparatus; a memory operatively coupled to the processing apparatus; a communication interface, operatively coupled to the processing apparatus; and an input/output interface, configured to receive sensor data comprising heart rate data, accelerometer data and audio data, wherein the processing apparatus is configured to determine if the heart rate data meets or exceeds a first predetermined threshold, activate the collection of accelerometer data and extract accelerometer data features if the heart rate exceeds the first threshold, determine if the heart rate data meets or exceeds a second predetermined threshold, activate the collection of audio data and extract audio data features if the heart rate data meets or exceeds the second predetermined threshold, determine if the audio data meets or exceeds a predetermined audio threshold, and transmit an alert indicating the detection of an onset ASD episode, based on the extracted audio data features, the extracted accelerometer data features and the heart rate data.

In some illustrative embodiments, a processor-based method is disclosed for detecting and alerting onset Autism Spectrum Disorder (ASD) in a device, comprising: receiving, at an input/output interface, sensor data comprising heart rate data; determining, in a processing apparatus, if the heart rate data meets or exceeds a first predetermined threshold; activating, via the processing apparatus, the collection of accelerometer data and extracting accelerometer data features if the heart rate exceeds the first threshold, determining, via the processing apparatus, if the heart rate data meets or exceeds a second predetermined threshold, activating, via the processing apparatus, the collection of audio data and extract audio data features if the heart rate data meets or exceeds the second predetermined threshold, determining, via the processing apparatus, if the audio data meets or exceeds a predetermined audio threshold, and transmitting, via a communications interface coupled to the processing apparatus, an alert indicating the detection of an onset ASD episode, based on the extracted audio data features, the extracted accelerometer data features and the heart rate data.

In some illustrative embodiments, a system is disclosed for detecting and alerting onset Autism Spectrum Disorder (ASD), comprising: a processing apparatus; a memory operatively coupled to the processing apparatus; a communication interface, operatively coupled to the processing apparatus; and an input/output interface, configured to receive sensor data comprising heart rate data, accelerometer data and audio data, wherein the processing apparatus is configured to activate the collection of accelerometer data and extract accelerometer data features comprising frequency components if the heart rate exceeds a first threshold, activate the collection of audio data and extract audio data features comprising frequency components if the heart rate data meets or exceeds a second predetermined threshold, determine if the audio data meets or exceeds a predetermined audio threshold comprising frequency characteristics, and transmit an alert indicating the detection of an onset ASD episode, based on the extracted audio data features, the extracted accelerometer data features, and the heart rate data.

BRIEF DESCRIPTION OF THE FIGURES

The present invention is illustrated by way of example and not limitation in the figures of the accompanying drawings, in which like references indicate similar elements and in which.

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

Figure 1:
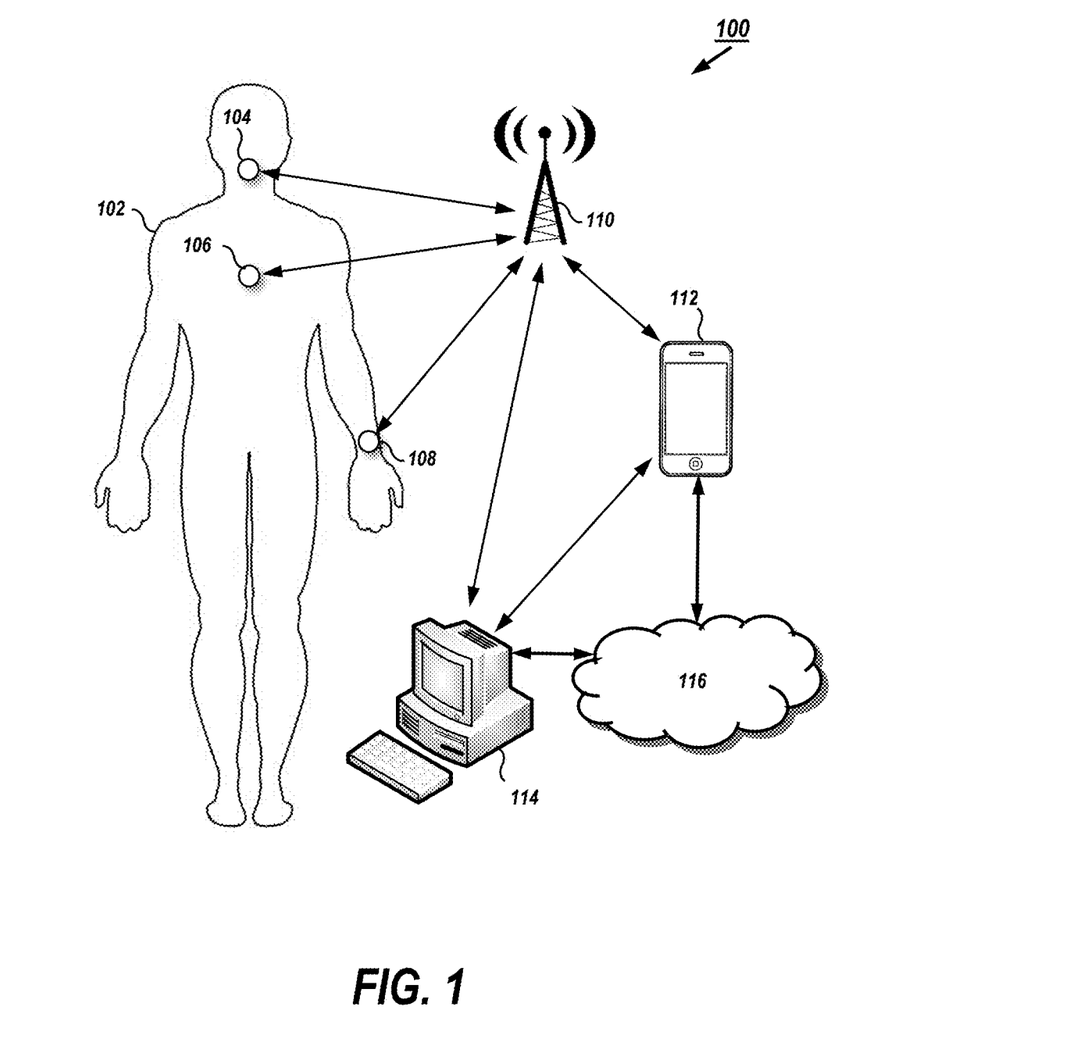
FIG. 1 illustrates a systematic overview of a wireless ASD monitoring system including sensors, a portable device, and a processing apparatus communicatively coupled to a network under an illustrative embodiment.

Turning to FIG. 1, a system 100 is shown for collecting and processing data from one or more sensors (104-116) communicatively coupled to the body of a user 102. In this example, sensor 108 may be an accelerometer sensor, which is known in the art. Generally speaking, an accelerometer is a device that measures the acceleration (or rate of change of velocity) of a body in its own instantaneous rest frame. Sensor 108 may be configured using a single- and/or multi-axis models of accelerometer to detect magnitude and direction of the proper acceleration, as a vector quantity, and can be used to sense orientation (because direction of weight changes), coordinate acceleration, vibration, shock, and falling in a resistive medium (a case where the proper acceleration changes, since it starts at zero, then increases). In an illustrative embodiment, sensor 108 may be configured as a micromachined microelectromechanical systems (MEMS) accelerometer, configured with suitable memory, processing, and a transmitter to process and transmit raw sensor data.

Sensor 106 may be configured as a heart rate monitor, which is known in the art. Sensor 106 may comprise a transmitter, worn on a chest strap, wrist strap, ankle strap, or any other suitable configuration, and a receiver, where, when a heartbeat is detected, a radio signal is transmitted, which the sensor receiver uses to determine a current heart rate. This signal can be a simple radio pulse or a unique coded signal from the chest strap (such as Bluetooth, ANT, or other low-power radio link); the latter prevents one user's receiver from using signals from other nearby transmitters (cross-talk interference). Alternately, sensor 106 may be configured to use optics to measure heart rate by measuring changes in blood flow by shining a light from an LED in the sensor through the skin and measuring how it scatters off blood vessels. In addition to measuring the heart rate, devices using this technology are able to measure blood oxygen saturation (SpO2). Sensor 106 may also include a microprocessor and suitable memory, along with a transmitter/receiver to simultaneously monitor heart rate, oxygen saturation, and other parameters. These may include sensors such as accelerometers, gyroscopes, and GPS to detect speed, location and distance.

Sensor 104 may comprise an audio sensor, which is generally known in the art. Sensor 104 may be configured as a microphone apparatus, configured to detect atmospheric vibrations that are perceived as sound. In an illustrative embodiment, sensor 104 is configured to detect frequencies in a broader range than possible by the human ear. Also, sensor 104 may be configured with a microprocessor and suitable memory, along with a transmitter receiver to process and transmit the raw audio data. In some illustrative embodiments, sensors 104-108 may be separate sensors, each with their own processing and transmitting apparatuses. In some illustrative embodiments, sensors 104-108 may be combined with each other in part, or combined together as one device. Sensors 104-108 may be configured to be physically worn on the body, or may be incorporated as peripheral devices on portable device 112, which may be a smart phone, tablet, or any suitable processing device known in the art. Each of sensors 104-108 are configured to transmit and receive data via wireless node 110 using a suitable wireless communication protocol. Node 110 is further configured to communicate data with portable device 112 and/or processing device 114. Portable device 112 may also communicate with processing device 114, and together they may individually communicate over computer network 116.

Figure 2:
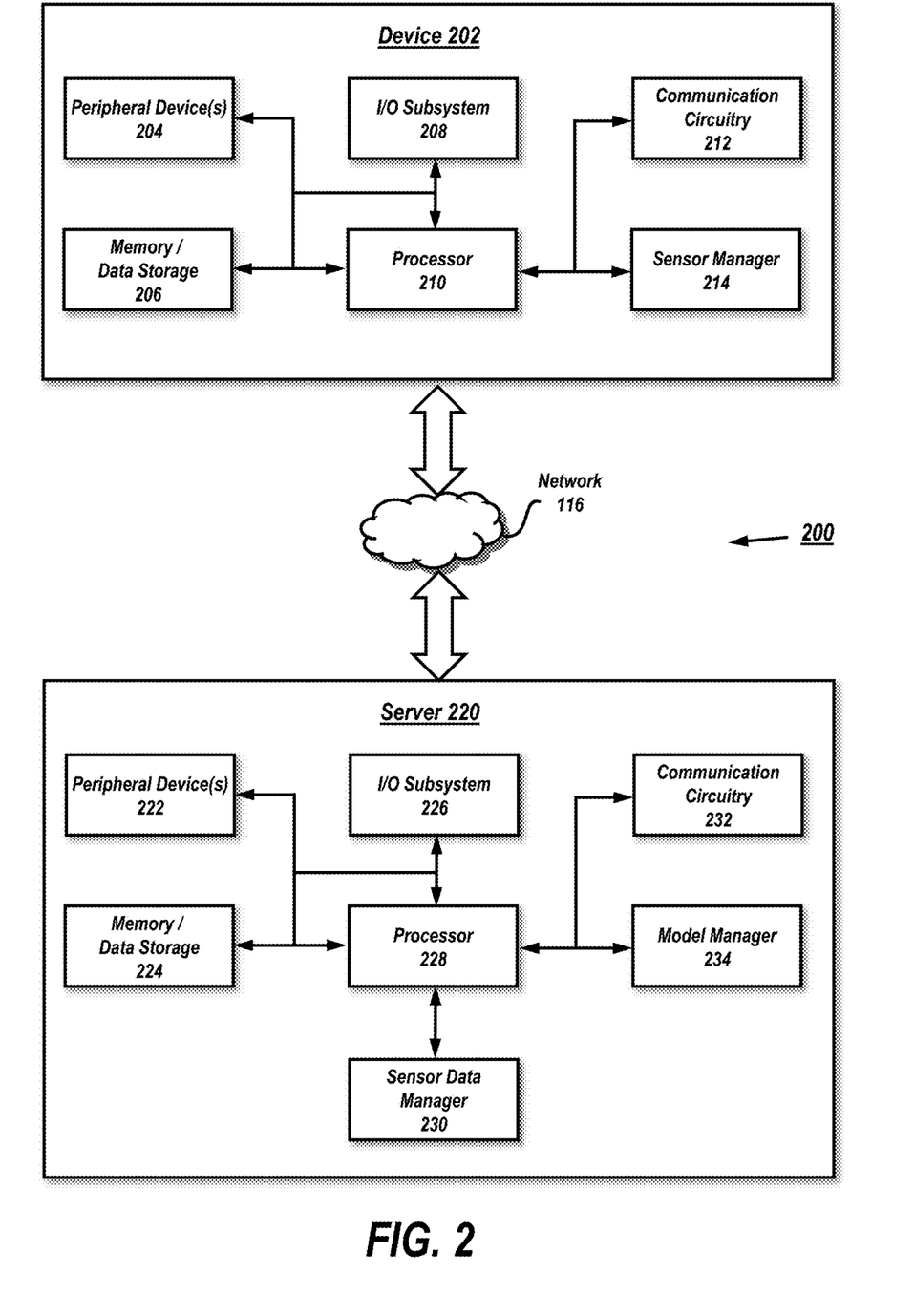
FIG. 2 schematically illustrates an operating environment for a portable device and a server communicatively coupled to a network for processing ASD data under an illustrative embodiment.

FIG. 2 shows an operating environment for system 200 that includes a processing device 202 (e.g., portable device 112 of FIG. 1) and a server 220 communicating via the network 116, wherein the system is configured to process sensor data under an illustrative embodiment. In the illustrative embodiment, the processing device 202 includes a processor 210 or processor circuit, one or more peripheral devices 204, memory/data storage 206, communication circuity 212, and a sensor manager 214. Sensor manager 214 may be configured to process and/or manage sensor data received from any of the sensors described above in connection with FIG. 1. The sensor manager 214 may be incorporated into memory/data storage 206 with or without a secure memory area, or may be a dedicated component, or incorporated into the processor 210. Of course, processing device 202 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 206, or portions thereof, may be incorporated in the processor 210 in some embodiments.

The processor 210 may be embodied as any type of processor currently known or developed in the future and capable of performing the functions described herein. For example, the processor 210 may be embodied as a single or multi-core processor(s), digital signal processor, microcontroller, or other processor or processing/controlling circuit. Similarly, memory/data storage 206 may be embodied as any type of volatile or non-volatile memory or data storage currently known or developed in the future and capable of performing the functions described herein. In operation, memory/data storage 206 may store various data and software used during operation of the processing device 210 such as access permissions, access parameter data, operating systems, applications, programs, libraries, and drivers.

Memory/data storage 206 may be communicatively coupled to the processor 210 via an I/O subsystem 208, which may be embodied as circuitry and/or components to facilitate input/output operations with the processor 210, memory/data storage 206, and other components of the processing device 202. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 210, memory/data storage 206, and other components of the processing device 202, on a single integrated circuit chip.

The processing device 202 includes communication circuitry 212 (communication interface) that may include any number of devices and circuitry for enabling communications between processing device 202 and one or more other external electronic devices and/or systems. Similarly, peripheral devices 204 may include any number of additional input/output devices, interface devices, and/or other peripheral devices. The peripheral devices 204 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 220 may be embodied as any type of server (e.g., a web server, etc.) or similar computing device capable of performing the functions described herein. In the illustrative embodiment of FIG. 2 the server 220 includes a processor 228, an I/O subsystem 226, a memory/data storage 224, communication circuitry 232, and one or more peripheral devices 222. Components of the server 220 may be similar to the corresponding components of the processing device 202, the description of which is applicable to the corresponding components of server 220 and is not repeated herein for the purposes of brevity.

The communication circuitry 232 of the server 220 may include any number of devices and circuitry for enabling communications between the server 220 and the processing device 202. In some embodiments, the server 220 may also include one or more peripheral devices 222. Such peripheral devices 222 may include any number of additional input/output devices, interface devices, and/or other peripheral devices commonly associated with a server or computing device. The server 220 also includes a sensor data manager 230 that is configured to process sensor data from sensor manager 214. The processing from sensor data manager 230 may be configured as back-end processing, and/or may be configured to further process sensor data processed and/or pre-processed in sensor manager 214.

In the illustrated embodiment, communication between the server 220 and the processing device 202 takes place via a network 116 that may be operatively coupled to one or more network switches (not shown). In one embodiment, the network 116 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 202 and the communication circuitry 232 of the server 220 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 116 may include any number of additional devices, such as additional computers, routers, and switches, to facilitate communications between the processing device 202 and the server 220.

Figure 3:
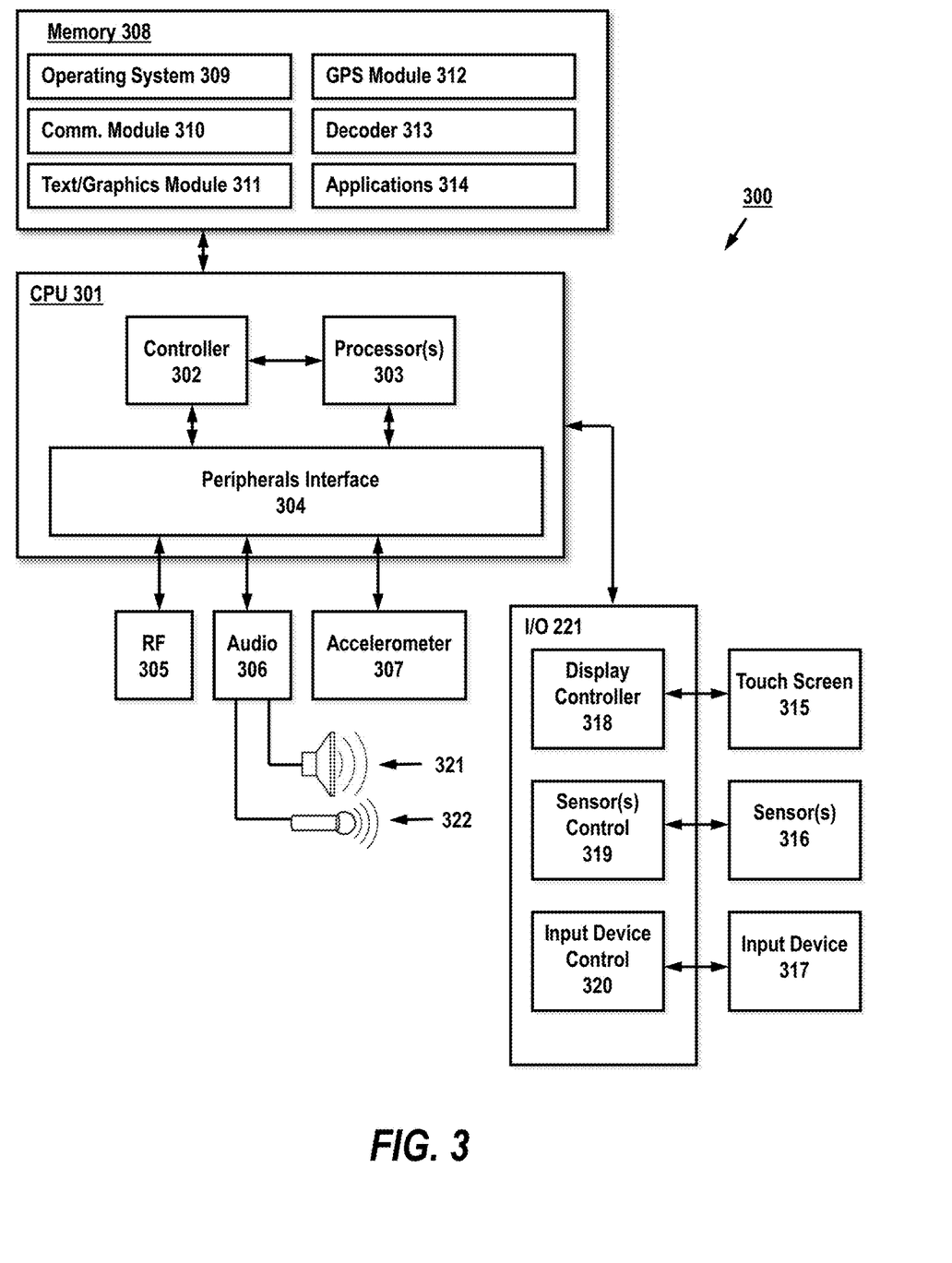
FIG. 3 schematically illustrates an operating environment for a portable device configured to process ASD data under an illustrative embodiment.

FIG. 3 is an exemplary embodiment of a portable computing device 300 (such as devices 202, 112), and may be a smart phone, tablet computer, laptop or the like. Device 300 may include a central processing unit (CPU) 301 (which may include one or more computer readable storage mediums), a memory controller 302, one or more processors 303, a peripherals interface 304, RF circuitry 305, audio circuitry 306, accelerometer 307, speaker 321, microphone 322, and input/output (I/O) subsystem 221 having display controller 318, control circuitry for one or more sensors 319 and input device control 320. These components may communicate over one or more communication buses or signal lines in device 300. It should be appreciated that device 300 is only one example of a portable multifunction device, and that device 300 may have more or fewer components than shown, may combine two or more components, or a may have a different configuration or arrangement of the components. The various components shown in FIG. 3 may be implemented in hardware or a combination of hardware and software, including one or more signal processing and/or application specific integrated circuits.

Memory (or storage) 308 may include high-speed random access memory (RAM) and may also include non-volatile memory, such as one or more magnetic disk storage devices, flash memory devices, or other non-volatile solid-state memory devices. Access to memory 308 by other components of the device 300, such as processor 303, and peripherals interface 304, may be controlled by the memory controller 302. Peripherals interface 304 couples the input and output peripherals of the device to the processor 303 and memory 308. The one or more processors 303 run or execute various software programs and/or sets of instructions stored in memory 308 to perform various functions for the device 300 and to process data. In some embodiments, the peripherals interface 304, processor(s) 303, decoder 313 and memory controller 302 may be implemented on a single chip, such as a chip 301. In other embodiments, they may be implemented on separate chips.

RF (radio frequency) circuitry 305 receives and sends RF signals, also known as electromagnetic signals. The RF circuitry 305 converts electrical signals to/from electromagnetic signals and communicates with communications networks and other communications devices via the electromagnetic signals. The RF circuitry 305 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 305 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 306, speaker 321, and microphone 322 provide an audio interface between a user and the device 300. Audio circuitry 306 may receive audio data from the peripherals interface 304, converts the audio data to an electrical signal, and transmits the electrical signal to speaker 321. The speaker 321 converts the electrical signal to human-audible sound waves. Audio circuitry 306 also receives electrical signals converted by the microphone 321 from sound waves, which may include utterances from a speaker. The audio circuitry 306 converts the electrical signal to audio data and transmits the audio data to the peripherals interface 304 for processing. Audio data may be retrieved from and/or transmitted to memory 308 and/or the RF circuitry 305 by peripherals interface 304. In some embodiments, audio circuitry 306 also includes a headset jack for providing an interface between the audio circuitry 306 and removable audio input/output peripherals, such as output-only headphones or a headset with both output (e.g., a headphone for one or both ears) and input (e.g., a microphone).

I/O subsystem 221 couples input/output peripherals on the device 300, such as touch screen 315, sensors 316 and other input/control devices 317, to the peripherals interface 304. The I/O subsystem 221 may include a display controller 318, sensor controllers 319, and one or more input controllers 320 for other input or control devices. The one or more input controllers 320 receive/send electrical signals from/to other input or control devices 317. The other input/control devices 317 may include physical buttons (e.g., push buttons, rocker buttons, etc.), dials, slider switches, joysticks, click wheels, and so forth. In some alternate embodiments, input controller(s) 320 may be coupled to any (or none) of the following: a keyboard, infrared port, USB port, and a pointer device such as a mouse, an up/down button for volume control of the speaker 321 and/or the microphone 322. Touch screen 315 may also be used to implement virtual or soft buttons and one or more soft keyboards.

Touch screen 315 provides an input interface and an output interface between the device and a user. Display controller 318 receives and/or sends electrical signals from/ to the touch screen 315. Touch screen 315 displays visual output to the user. The visual output may include graphics, text, icons, video, and any combination thereof. In some embodiments, some or all of the visual output may correspond to user-interface objects. Touch screen 315 has a touch-sensitive surface, sensor or set of sensors that accepts input from the user based on haptic and/or tactile contact. Touch screen 315 and display controller 318 (along with any associated modules and/or sets of instructions in memory 308) detect contact (and any movement or breaking of the contact) on the touch screen 315 and converts the detected contact into interaction with user-interface objects (e.g., one or more soft keys, icons, web pages or images) that are displayed on the touch screen. In an exemplary embodiment, a point orf contact between a touch screen 315 and the user corresponds to a finger of the user. Touch screen 215 may use LCD (liquid crystal display) technology, or LPD (light emitting polymer display) technology, although other display technologies may be used in other embodiments. Touch screen 315 and display controller 318 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 315.

Device 300 may also include one or more sensors 316 such as heart rate sensors, touch sensors, optical sensors that comprise charge-coupled device (CCD) or complementary metal-oxide semiconductor (CMOS) phototransistors. The optical sensor may capture still images or video, where the sensor is operated in conjunction with touch screen display 315. Device 300 may also include one or more accelerometers 307, which may be operatively coupled to peripherals interface 304. Alternately, the accelerometer 307 may be coupled to an input controller 320 in the I/O subsystem 221. The accelerometer is preferably configured to output accelerometer data in the x, y, and z axes.

In some illustrative embodiments, the software components stored in memory 308 may include an operating system 309, a communication module 310, a text/graphics module 311, a Global Positioning System (GPS) module 312, decoder 313 and applications 314. Operating system 309 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 310 facilitates communication with other devices over one or more external ports and also includes various software components for handling data received by the RF circuitry 305. An external port (e.g., Universal Serial Bus (USB), Firewire, etc.) may be provided and adapted for coupling directly to other devices or indirectly over a network (e.g., the Internet, wireless LAN, etc.).

Text/graphics module 311 includes various known software components for rendering and displaying graphics on the touch screen 315, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 312 determines the location of the device and provides this information for use in various applications. Applications 314 may include various modules, including health monitoring software, sensor software, navigation software, mapping, address books/contact list, email, instant messaging, and the like.

Figure 4A:
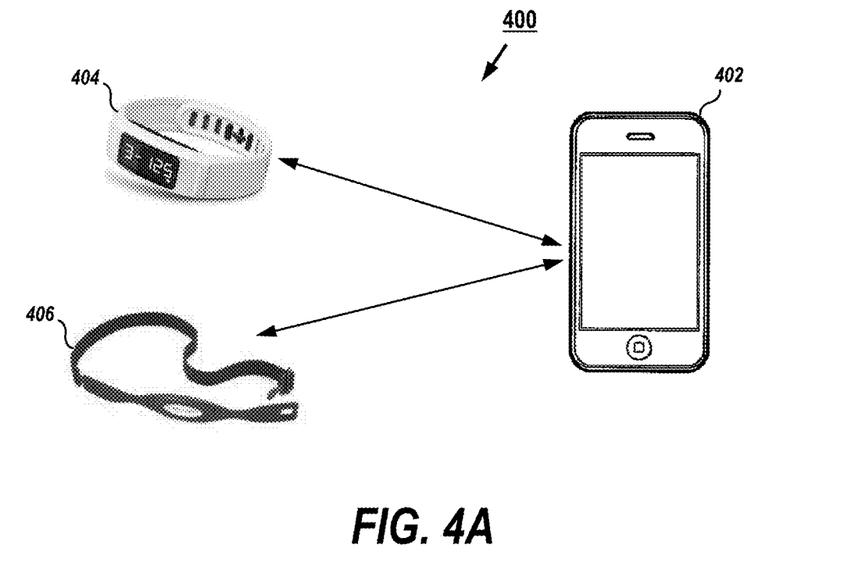
FIG. 4A shows a simplified example of a plurality of sensors wirelessly communicating with a portable device under an illustrative embodiment
Figure 4B:
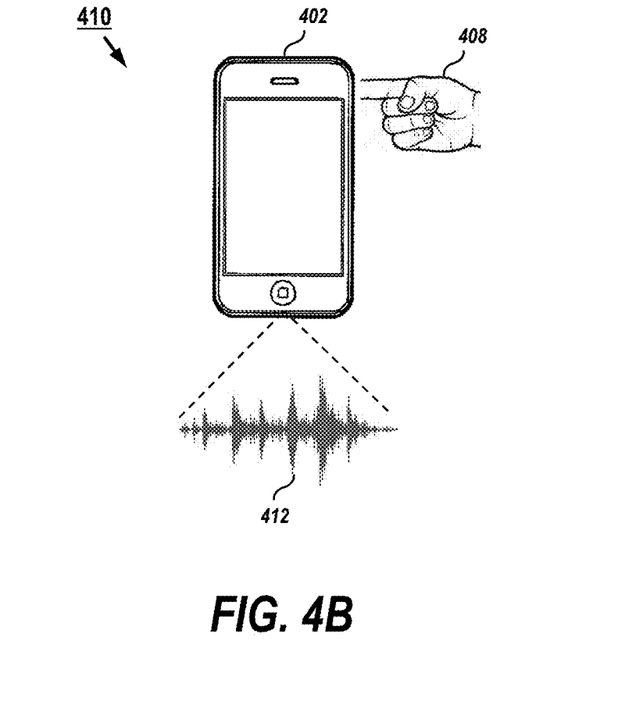
FIG. 4B shows another simplified example of a portable device utilizing phone sensors under an illustrative embodiment.

FIG. 4A shows a simplified example of a system arrangement 400, wherein a first sensor 404 and second sensor 406 communicate wirelessly with a portable device 402 under an illustrative embodiment. As explained herein, it is understood by those skilled in the art that the specific sensors named herein are merely for exemplary purposes, and that other sensors may be incorporated into the present disclosure. For example, perspiration sensors, blood glucose sensors, eye movement sensors and other suitable sensors are contemplated in the present disclosure. FIG. 4B shows another simplified example of a system arrangement 410 wherein the portable device 402 utilizes phone sensors under an illustrative embodiment. Here, a portable device 402 camera (not shown) may be utilized by a user to place a finger of a hand 408 over the camera lens to determine heart rate 412.

Figure 5:
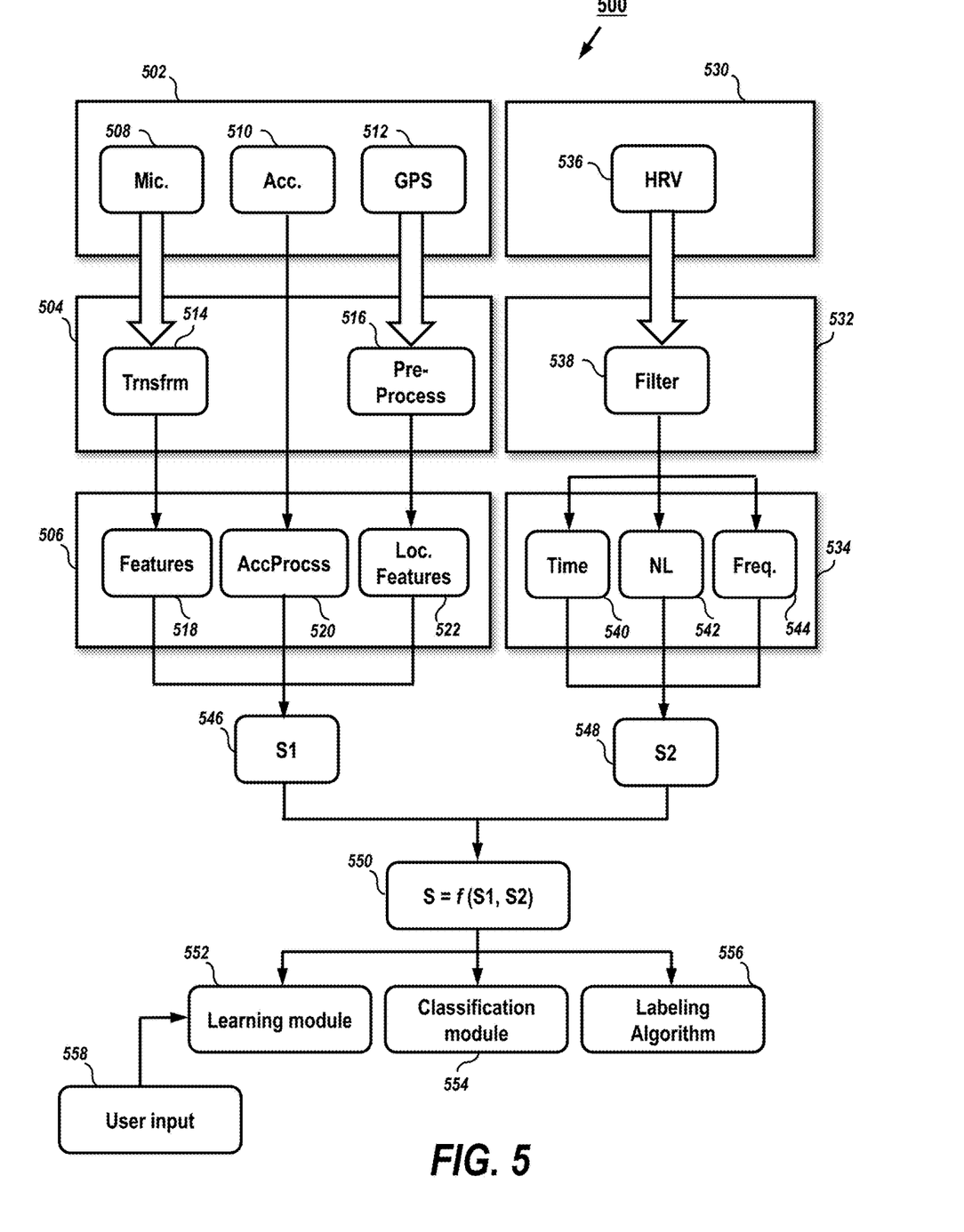
FIG. 5 shows an operating environment for processing sensor data from multiple sources in a portable device and providing a detection value, along with learning, classification and labeling algorithms under an illustrative embodiment.

FIG. 5 shows an operating environment 500 for processing sensor data from multiple sources in a portable device and providing a detection value, along with learning, classification and labeling algorithms under an illustrative embodiment. In this example, the operating environment is broken down into processing blocks 502-506 that may be configured to operate on a portable device (e.g., 202) and processing blocks 530-534 that may be configured to operate on a sensing device (e.g., 104-108). The processing blocks are tiered to provide sensing 502, pre-processing 504 and processing 506 for the portable device, and sensing 530, pre-processing 532 and processing 534 for the sensing device. Again, the operating environment 500 of FIG. 5 is merely one example, and other possible configurations are contemplated in the present disclosure.

Starting with portable device sensing block 502, ambient sound waves are captured in microphone 508, multi-axis accelerometer values are captured in accelerometer 510, and GPS coordinates are captured in GPS 512. The raw audio data from microphone 508 is transmitted to pre-processing block 504, in which the raw audio data is transformed into frequency components, described in greater detail below. Raw GPS data from GPS 512 may be transmitted to GPS pre-processing 516. In some illustrative embodiments, the GPS pre-processing block 516 may comprise a heuristic and/or temporal preprocessing on the GPS coordinates. Locations may be derived using a density-based clustering algorithm (DBSCAN). In some illustrative embodiments, GPS traces may be anonymized by shifting the absolute positions such that the centroid of the locations becomes the zero point of the coordinate system.

Turning to processing block 506, the illustrated sub-blocks may be configured for processing on a portable device (e.g., 112, 202) and/or processing device (e.g., 114). In this example, feature block 518 receives the transformed audio data from block 514, and performs feature extraction 518 on the audio to identify characteristics of the audio. In some illustrative embodiments, the audio feature extraction may be based on a Fast Fourier Transorm (FFT) algorithm that samples an audio signal over a period of time or space and divides it into its frequency components comprising single sinusoidal oscillations at distinct frequencies each with their own amplitude and phase. Dominant frequencies may be determined by measuring the divided signal over a predetermined time period. The FFT algorithm may be configured to calculate the discrete Fourier transform (DFT) of a sequence, or its inverse (IFFT). Fourier analysis may then be used to convert the signal from its original domain to a representation in the frequency domain, and vice versa. The FFT rapidly computes such transformations by factorizing the DFT matrix into a product of sparse (mostly zero) factors. As a result, it manages to reduce the complexity of computing the DFT from $O(n^2)$, which arises if one simply applies the definition of DFT, to $O((n)\log n)$, where n is the data size.

In some illustrative embodiments, audio feature extraction 518 may be based on a mel-frequency cepstrum (MFC), which represents the short-term power spectrum of a sound received from microphone 322, based on a linear cosine transform of a log power spectrum on a nonlinear mel scale of frequency. The MFC may be based on collective mel-frequency cepstral coefficients (MFCCs) derived from a type of cepstral representation of the audio. The difference between the cepstrum and the mel-frequency cepstrum is that in the MFC, the frequency bands are equally spaced on the mel scale, which computationally approximates the human auditory system's response more closely than the linearly-spaced frequency bands used in the normal cepstrum. This frequency warping can allow for better representation of sound, for example, on processing human speech. MFCCs may be derived by taking the Fourier transform of (a windowed excerpt of) a signal, where the powers of the spectrum obtained are mapped onto the mel scale, using triangular overlapping windows. The logs of the powers are taken at each of the mel frequencies, and the discrete cosine transform is taken of the list of mel log powers, as if it were a signal. The MFCCs would be the amplitudes of the resulting spectrum. Of course, those skilled in the art will appreciate that there may be variations on this process, such as using differences in the shape or spacing of the windows used to map the scale, or the addition of dynamics features such as "delta" and "delta-delta" (first- and second-order frame-to-frame difference) coefficients.

In some illustrative embodiments, it has been found that a non-stationary harmonic chirp model is particularly effective at modeling non-stationary signals, such as those likely to be produced by an ASD patient at the onset of an episode. In an example, a parametric time-varying model may be used to capture the linear evolution of the frequency of sinusoidal components. Here, characteristics such as the complex slope, introduced to capture variations of the harmonic components, can be decomposed into two terms, one for frequency adjustment and the other for the amplitude slope. This model may further be extended by a second order complex polynomial for each harmonic component. Accordingly, an overall estimation procedure may be performed, based on the minimization of a Least Square criterion, where model parameters may be refined using iteration in order to estimate the different sinusoidal components. Such a configuration may effectively track the linear evolution of the frequency of each sinusoidal component independently. Furthermore, the model can account for errors in the initial estimates of the sinusoidal component frequencies.

Turning to block 520, the accelerometer processing may implement an Artificial Neural Network (ANN) that receives as input the raw data acquired from the accelerometer, and extracts features from the accelerometer data, including, but not limited to, mean along z-axis, maximum, minimum, standard deviation and Root Mean Square (RMS) from the magnitude of the acceleration, average of peak frequency (APF), standard deviation, RMS, maximum and minimum along x-axis, y-axis and z-axis, and correlation between z-axis and y-axis. Features extracted from the magnitude of the acceleration include, but are not limited to, mean, standard deviation, cross-axis signals correlation, Fast Fourier Transform (FFT) spectral energy, frequency domain entropy and log of FFT, and implements the Naïve Bayes, C4.5 Decision Tree, K-Nearest Neighbor (KNN), and SVM methods. Location features block 522 performs the aforementioned heuristic and/or temporal preprocessing on the GPS coordinates and may derive location using DBSCAN or other suitable algorithm.

Turning to sensing block 530, a heart rate monitor sensor 536 receives the raw heart rate data, which is forwarded to pre-processing block 532, where filer 538 filters the raw data and provides the filtered data to processing block 534 that comprises a plurality of feature extracting blocks. Time domain features block 540 may include features including, but not limited to, mean value of variation of the beat-to-beat (RR) intervals (mean RR), standard deviation of RR intervals (SDNN), root-mean-square successive difference of RR intervals (RMSSD), number of successive difference of RR intervals which differ by more than 50 ms expressed as a percentage of total RR intervals (pNN50), and geometric measures, including the total number of RR intervals divided by the height of the histogram of all RR intervals measured on a scale with bins of $\frac{1}{128}$s (HRV index) and the triangular interpolation of RR interval histogram (TINN).

Nonlinear Features Approximate entropy (ApEn) may be utilized in block 542 to measure the complexity or irregularity of the signal, where large values of ApEn indicate high irregularity, and smaller values of ApEn indicate a more regular signal. The fast RR variability in the HRV data (SD1) may also be determined along with the long-term variability (SD2), where SD1 and SD2 may be considered as coefficients of the Poincoir plot. SD1/SD2 may be processed as the ratio of short interval variation to the long interval variation.

Frequency Domain Features may be processed in block 544 by estimating the power spectral density of the RR intervals using the Lomb-Scargle periodogram since this algorithm is particularly advantageous with time series that are not necessarily evenly spaced. The spectrum may be divided into a plurality of frequency bands, such as very low frequency (VLV), 0.01-0.04 Hz; low frequency (LF), 0.04-0.15 Hz; and high frequency (HF), 0.15-0.4 Hz. In some illustrative embodiments, the features used are the normalized values of LF, HF, and the ratio of LF and HF (LF/HF). The ratio LF/HF is not only useful as a feature for detecting stress, but is also very important to differentiate between sleep stages.

The outputs of processing block 506 may be combined to form a global sensor output S1 546, while the output of processing block 534 may be combined to form another global sensor output S2. The global sensor outputs S1, s2 may further be used to formulate a total sensor output value S that is configured as a function of outputs S1 and S2. The global sensor outputs S1, S2 may be configured as string value that may or may not include partitions for each respective data portion (e.g., 518-522, 540-544), however the total and global sensor outputs should preferably include markers or flags that allow the system to process individual portions of each total and/or global sensor output as required.

The total sensor output S 550 may then be used as an input to learning module 552, classification module 554 and labeling module 556 in order to classify and label various sensor outputs and sensor output combinations. Accordingly, when certain sensor conditions occur and subsequently change, the blocks 552-556 may adapt to those changes and provide new and/or updated context to the sensor outputs. In some illustrative embodiments, the learning module 552 may include a user input 558 (such as 315, 317 of FIG. 3) that allows a user to manually provide an input to the device and/or system. This configuration may be advantageous for obtaining manual confirmation from the user when a sensor output condition is detected. In one example, after a sensor output condition is detected, a processor (e.g., CPU 301) may display the condition to a user, along with a request for the user to verify the sensor condition. Once the sensor condition is verified or rejected, the learning module 552 may update its settings accordingly to improve accuracy.

Figure 6:
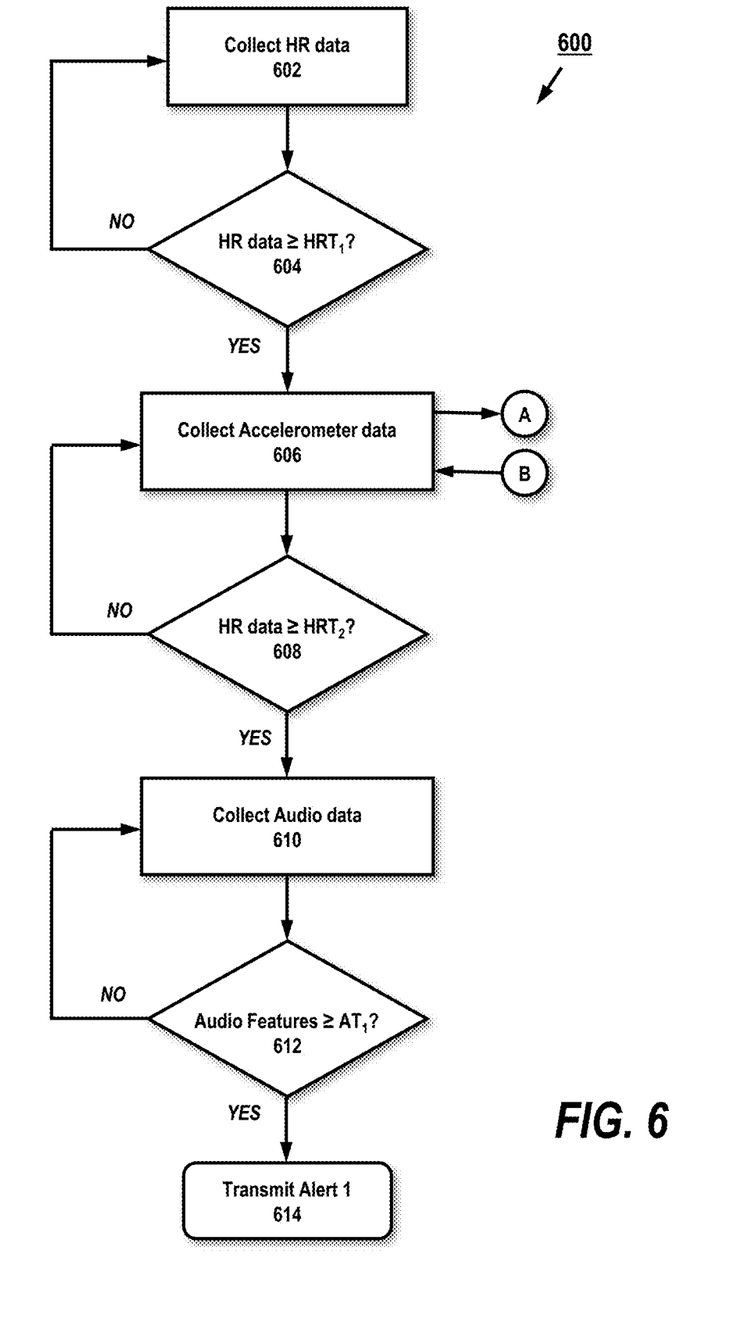
FIG. 6 shows a simplified process for collecting and processing heart rate data, accelerometer data, and audio data in a portable device to detect and alert for a state of ASD under an illustrative embodiment.

FIG. 6 shows a process 600 for collecting and processing heart rate data, accelerometer data, and audio data in a portable device to detect and alert for a state of ASD under an illustrative embodiment. In block 602, the device (e.g., 402) collects heart rate data utilizing any of the techniques disclosed herein. In decision block 604, the device determines if the heart rate data exceeds a predetermined threshold ($HRT_1$). If it does not ("NO"), the process 600 continues to collect heart rate data in block 602. In some illustrative embodiments, the collection of heart rate data may be continuous, or it may be periodic, over predetermined periods of time. In some illustrative embodiments, the collection of heart rate data may be triggered by the activation of another sensor (e.g., light sensor, accelerometer). If, in decision block 604, the device determines that the heart rate exceeds the predetermined threshold, the device (e.g., 402) begins to collect accelerometer data in block 606. In decision block 608, the device (e.g., 402) determines if the heart rate data exceeds a second threshold ($HRT_2$). If not ("NO"), the device (e.g., 402) continues to collect accelerometer data in block 606. If the heart rate is determined to exceed the second threshold ($HRT_2$) ("YES"), the device (e.g., 402) begins collecting audio data (e.g., via microphone 322) in block 610 to extract features and determine audio characteristics. In decision block 612, the device determines if the audio features meet or exceed an audio threshold ($AT_1$). In some illustrative embodiment, this threshold is based on frequency and/or amplitude characteristics of the transformed audio. In some illustrative embodiments, the threshold may be based on transformed audio coefficients, and/or slope and/or variations of harmonic components. If the device determines that the audio features do not exceed the audio threshold ("NO"), the process 500 then continues to collect audio data 610. If, however, the device determines in block 612 that the audio features exceed the threshold ("YES"), the device detects an onset ASD episode and transmits an alert in block 614.

It should be understood by those skilled in the art that the process of FIG. 6 may be modified to deactivate certain features if previously-exceeded thresholds fall back into compliance (i.e., fall below the threshold). For example, if the device is collecting audio data in block 610 and the detected heart rate falls below the second threshold ($HRT_2$), the device will stop collecting audio data. Similarly, if the detected heart rate continues to fall below the first threshold ($HRT_1$), the device may stop collecting accelerometer data. It should also be understood by those skilled in the art that the order of data collections (606, 610) may be altered or reversed, and that audio data may be collected in block 606, while accelerometer data may be collected in block 610.

Figure 7:
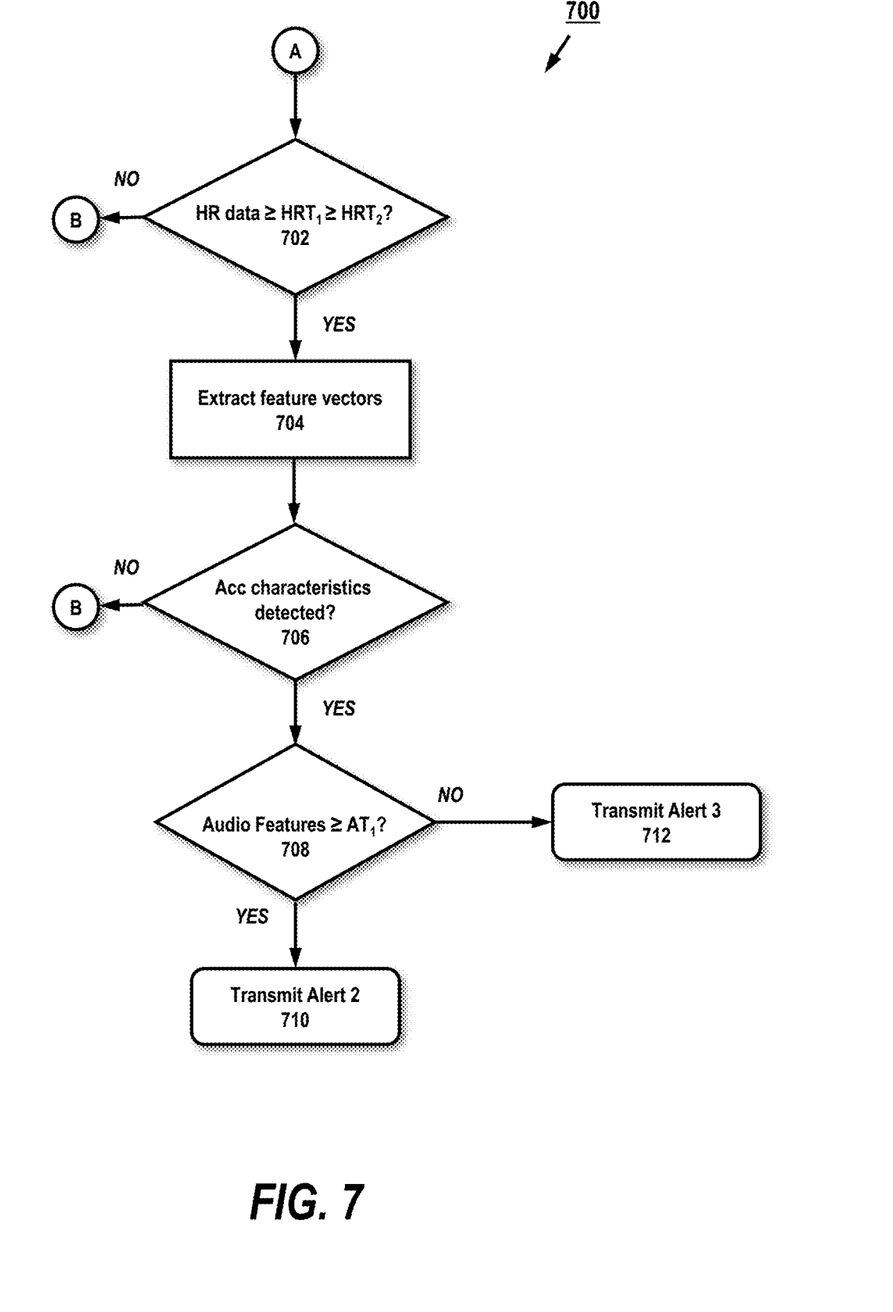
FIG. 7 shows a process for extracting feature vectors for accelerometer data based on hear rate conditions, and determining audio characteristics for detecting and alerting for a state of ASD under an illustrative embodiment.

FIG. 7 shows a process 700 for extracting feature vectors for accelerometer data based on heart rate conditions, and determining audio characteristics for detecting and alerting for a state of ASD under an illustrative embodiment. In some illustrative embodiments, there may be instances where heart rate data needs to be considered at or in between multiple heart rate thresholds. In the process 700, after accelerometer data is collected ("A", see 606), decision block 702 determines if the heart rate is between a plurality of heart rate thresholds ($HRT_1$, $HRT_2$). If not ("NO"), the process returns ("B") to collecting accelerometer data (606). If the heart rate is within a specific heart rate band ("YES") the device (e.g., 402) extracts accelerometer feature vectors in block 704. In decision block 706, the device determines if predetermined accelerometer feature characteristics are present. If not ("NO"), the process returns ("B") to collecting accelerometer data 606. If the predetermined accelerometer feature characteristics are present ("YES"), the process 500 then moves to decision block 708, where the device determines if audio features are greater than a predetermined audio threshold ($AT_1$) 708. If not, ("NO") the process 500 transmits an alert in block 712. If the audio features are greater that the predetermined audio threshold ("YES"), then the process transmits an alert in block 710.

It should be understood by those skilled in the art that the alerts disclosed in blocks 614, 710 and/or 712 are pursuant to a device detecting the onset of an ASD episode. In other words, a device may be configured to collect and process sensor data and transform it into a tangible estimation of an ASD episode. This technical result advantageously allows for individuals to monitor and alert ASD patients, their friends and/or relatives, as well as health care service providers that may be associated with the ASD patient.

In some illustrative embodiments, the system may use filters so that alerts are selectively transmitted, based on a magnitude and/or frequency of sensor values. The filter may be advantageously used so that the user/patient, friends, relatives and/or service providers are not inundated with multiple alerts for a single episode. A timer may also be used that is set to a default value that can be changed using the learning module 552.

Also, using the technologies and techniques disclosed herein, conventional operations on devices monitoring ASD are improved, by allowing the device to sense, collect and process data in a tiered fashion, using co-dependent sensor values (e.g., heart rate, accelerometer, audio) to determine the timing, order and the level of sensing, thus reducing the overall processing overhead and strain placed on a battery.

In addition to the above disclosure, in some illustrative embodiments, sensor thresholds may be made dependent on a detected location for a device. In some illustrative embodiments, GPS coordinates may be labeled to determine location characteristics. For example, a locations may be specific to the user (e.g., "home", "work", "school", mother's house", etc.), or may be generically specified by type (e.g., "supermarket", "movie theater", "restaurant", "car wash", etc.). In some illustrative embodiments, the location may be tied to a specific merchant for the location (e.g., "Best Buy", "McDonalds", etc.). During operation, the system (e.g., 100, 200) may initially begin with a default set of thresholds, where each threshold may be different and specific to a location and/or location characteristic. In some illustrative embodiments, thresholds may be the same for locations having similar location characteristics.

As the operating environment (e.g., 500) continues operation, the modules 552-556 may "learn" the effects these locations may have on a user and adjust sensor parameters and thresholds for any sensor accordingly. For example, if a user's GPS location shows them to be at a gym, the heart rate and accelerometer parameters/thresholds may be adjusted upwards to reflect the physical activity being performed by the user. Because the sensor thresholds are increased, this reduces the possibility of detecting false positives. Similarly, if a user has been previously detected to have had one or more episodes at a specific location, the sensor thresholds may be adjusted downward in order to allow the system to detect onset ASD episodes earlier. In some illustrative embodiments, sensor thresholds may be moved up and/or down independently of each other, depending on the application.

Figure 8:
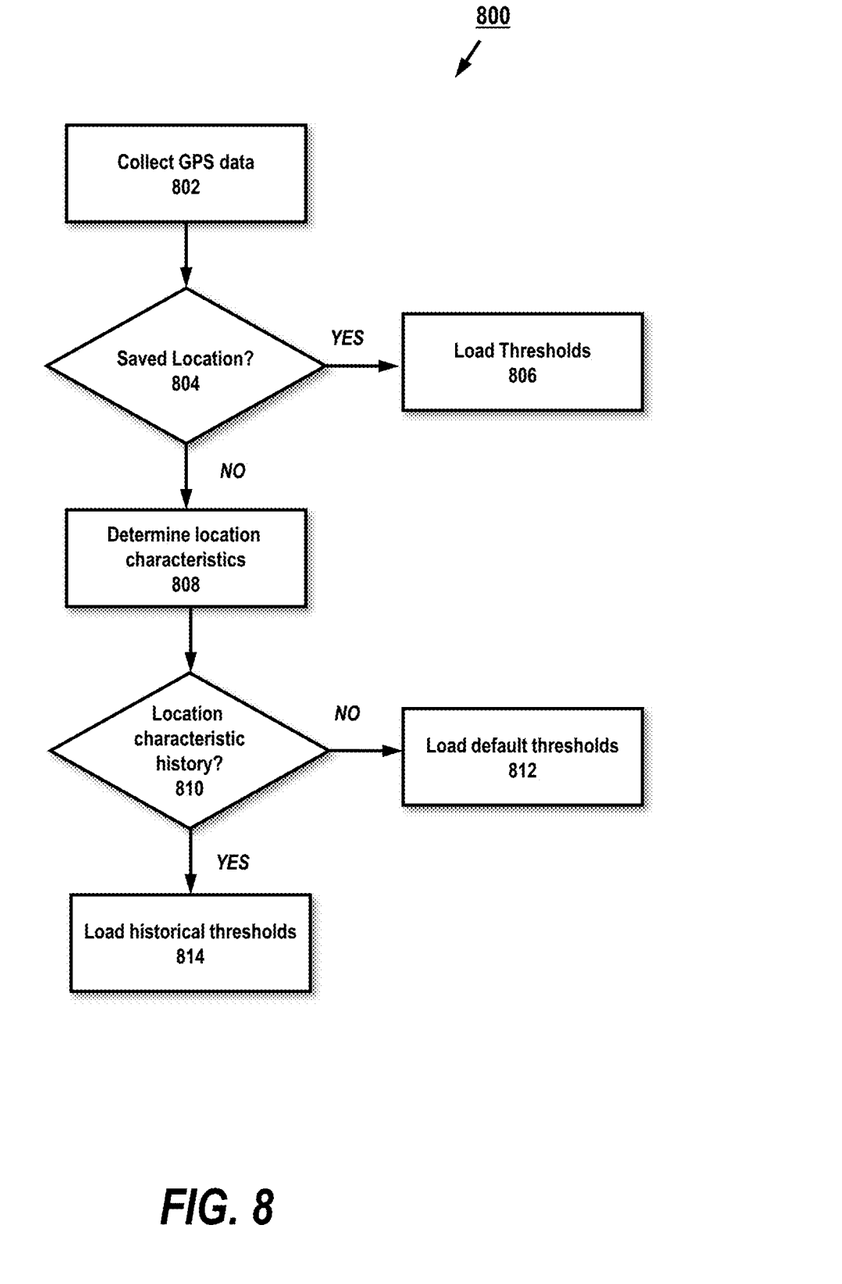
FIG. 8 shows a process for collecting and processing global positioning system (GPS) data for loading thresholds for use in sensor data processing under an illustrative embodiment.

FIG. 8 shows a process 800 for collecting and processing global positioning system (GPS) data for loading thresholds for use in sensor data processing under an illustrative embodiment. In block 802 the device may collect GPS data. In decision block 804, the device determines if the GPS data reflects a saved location. If the location is saved ("YES"), the process 800 loads thresholds in block 806 that are associated with the saved location. If the location is not saved ("NO"), the process 800 moves to decision block 810 to see if there is a location characteristic history. If not ("NO"), the system loads the default thresholds in block 812. If a location characteristic history exists ("YES"), the system loads historical thresholds for the associated location characteristic in block 814.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A portable system for tiered, co-dependent sensor activation for monitoring onset Autism Spectrum Disorder (ASD), comprising:
   a processing apparatus;
   a memory operatively coupled to the processing apparatus;
   a communication interface, operatively coupled to the processing apparatus; and
   an input/output interface, configured to receive sensor data comprising heart rate sensor data, accelerometer sensor data and audio sensor data,
   wherein the processing apparatus is configured to
      determine if the heart rate sensor data meets or exceeds a first predetermined threshold,
      activate the collection of accelerometer sensor data and extract accelerometer data features if the heart rate exceeds the first threshold,
      determine if the heart rate sensor data meets or exceeds a second predetermined threshold,
      activate the collection of audio sensor data and extract audio data features if the heart rate sensor data meets or exceeds the second predetermined threshold,
      determine if the audio sensor data meets or exceeds a predetermined audio threshold, and
      transmit an alert indicating the detection of an onset ASD episode, based on the extracted audio data features, the extracted accelerometer data features and the heart rate data.

2. The system of claim 1, wherein the processing apparatus is further configured to
   process GPS data to determine a location of the processing apparatus; and
   set at least one of the first predetermined threshold and the second predetermined threshold based on the determined location.

3. The system of claim 1, wherein the heart rate data comprises time domain features and frequency domain features.

4. The system of claim 1 wherein the processing apparatus is configured to extract accelerometer data features utilizing an artificial neural network (ANN).

5. The system of claim 1, wherein the processing apparatus is configured to extract audio data features by transforming ambient audio into frequency components.

6. The system of claim 5, wherein the processing apparatus is configured to extract audio data features utilizing a harmonic chip model applied to the frequency components.

7. The system of claim 1, wherein the input/output interface is configured to receive a feedback in response to transmitting the alert, and wherein the processing apparatus is configured to modify at least one of the first predetermined threshold and second predetermined threshold based on the received feedback.

8. A processor-based method for tiered, co-dependent sensor activation for monitoring onset Autism Spectrum Disorder (ASD) in a portable device, comprising:
receiving, at an input/output interface, sensor data comprising heart rate sensor data;
determining, in a processing apparatus, if the heart rate sensor data meets or exceeds a first predetermined threshold;
activating, via the processing apparatus, the collection of accelerometer sensor data and extracting accelerometer data features if the heart rate exceeds the first threshold,
determining, via the processing apparatus, if the heart rate sensor data meets or exceeds a second predetermined threshold,
activating, via the processing apparatus, the collection of audio sensor data and extract audio data features if the heart rate sensor data meets or exceeds the second predetermined threshold,
determining, via the processing apparatus, if the audio sensor data meets or exceeds a predetermined audio threshold, and
transmitting, via a communications interface coupled to the processing apparatus, an alert indicating the detection of an onset ASD episode, based on the extracted audio data features, the extracted accelerometer data features and the heart rate data.

9. The method of claim 8, further comprising:
process, via the processing apparatus, GPS data to determine a location of the device; and
setting, via the processing apparatus, at least one of the first predetermined threshold and the second predetermined threshold based on the determined location.

10. The method of claim 8, wherein the heart rate data comprises time domain features and frequency domain features.

11. The method of claim 8 wherein extracting the accelerometer data features comprises utilizing an artificial neural network (ANN).

12. The method of claim 8, wherein extracting audio data features comprises transforming ambient audio into frequency components.

13. The method of claim 12, wherein extracting audio data features comprises utilizing a harmonic chip model applied to the frequency components.

14. The method of claim 8, further comprising:
receiving, via an input-output interface, a feedback in response to transmitting the alert; and
modifying, via the processing apparatus, at least one of the first predetermined threshold and second predetermined threshold based on the received feedback.

15. A portable system for tiered, co-dependent sensor activation for monitoring onset Autism Spectrum Disorder (ASD), comprising:
a processing apparatus;
a memory operatively coupled to the processing apparatus;
a communication interface, operatively coupled to the processing apparatus; and
an input/output interface, configured to receive sensor data comprising heart rate sensor data, accelerometer sensor data and audio sensor data,
wherein the processing apparatus is configured to
activate the collection of accelerometer sensor data and extract accelerometer data features comprising frequency components if the heart rate exceeds a first threshold,
activate the collection of audio sensor data and extract audio data features comprising frequency components if the heart rate sensor data meets or exceeds a second predetermined threshold,
determine if the audio sensor data meets or exceeds a predetermined audio threshold comprising frequency characteristics, and
transmit an alert indicating the detection of an onset ASD episode, based on the extracted audio data features, the extracted accelerometer data features and the heart rate data.

16. The system of claim 15, wherein the processing apparatus is further configured to
process GPS data to determine a location of the processing apparatus; and
set at least one of the first predetermined threshold and the second predetermined threshold based on the determined location.

17. The system of claim 15, wherein the heart rate data comprises time domain features and frequency domain features.

18. The system of claim 15, wherein the processing apparatus is configured to extract accelerometer data features utilizing an artificial neural network (ANN).

19. The system of claim 15, wherein the processing apparatus is configured to extract audio data features by transforming ambient audio into frequency components.

20. The system of claim 15, wherein the input/output interface is configured to receive a feedback in response to transmitting the alert, and wherein the processing apparatus is configured to modify at least one of the first predetermined threshold and second predetermined threshold based on the received feedback.

* * * * *